United States Patent [19]
Kunkle, Jr.

[11] Patent Number: 5,955,436
[45] Date of Patent: Sep. 21, 1999

[54] USE OF PLATELET DERIVED GROWTH FACTOR TO ENHANCE WOUND HEALING

[75] Inventor: H. Melvin Kunkle, Jr., Mansfield, Tex.

[73] Assignee: Alcon Laboratories, Inc., Fort Worth, Tex.

[21] Appl. No.: 08/358,646

[22] Filed: Dec. 19, 1994

Related U.S. Application Data

[63] Continuation of application No. 08/220,947, Mar. 31, 1994, abandoned, which is a continuation of application No. 07/738,760, Aug. 1, 1991, abandoned, which is a continuation-in-part of application No. 07/616,281, Nov. 20, 1990, abandoned.

[51] Int. Cl.[6] .......................... A61K 37/00; A61K 37/18
[52] U.S. Cl. .................................. 514/21; 514/2; 514/912
[58] Field of Search .................................. 514/2, 21, 912

[56] References Cited

U.S. PATENT DOCUMENTS

| | | | |
|---|---|---|---|
| 4,760,131 | 7/1988 | Sundsmo et al. | 530/356 |
| 4,861,757 | 8/1989 | Antoniades et al. | 514/21 |
| 4,874,746 | 10/1989 | Antoniades et al. | 514/21 |
| 4,981,841 | 1/1991 | Gibson | 514/2 |
| 4,983,580 | 1/1991 | Gibson | 514/2 |

FOREIGN PATENT DOCUMENTS

| | | |
|---|---|---|
| 312 208 | 9/1988 | European Pat. Off. . |
| 322 249 | 12/1988 | European Pat. Off. . |

OTHER PUBLICATIONS

D. Gospodarowicz and L. Giguere, *Cell Biology of the Eye* (ed. David S. McDevitt), Ch. 3, New York: Academic Press, 1982.

Ross, R. et al., "The Biology of Platelet–Derived Growth Factor," *Cell*, 46:155–169 (1986).

Lynch, S. E. et al., "Role of platelet–derived growth factor in wound healing: Synergistic effects with other growth factors," *PNAS*, 84:7696–7700 (1987).

Ksander, G. A., "Exogenous Growth Factors in Dermal Wound Healing," *Ann. Rep. Med. Chem.*, 24:223–232 (1989).

Nakada, S. et al. "Effect of PDGF, IGF and EGF on Corneal Epithelial Wound Healing and Reinnervation," *Invest. Ophthal. Vis. Sci.*, 31(4):54 (1990).

Chiron Corp. Monograph on Epidermal Growth Factor (1989).

Harvey, A. K. et al., "Chemotaxis of Rat Retinal Glia to Growth Factors Found in Repairing Wounds," *Invest. Ophthalmol. Vis. Sci.*, 28:1092–1099 (1987).

Courty, J. et al., "Propriétés in vitro de quelques facteurs de croissance et effets in vivo," *Biochimi*, 66:419–428 (1984).

*Primary Examiner*—Zohreh Fay
*Attorney, Agent, or Firm*—Barry L. Copeland

[57] ABSTRACT

Disclosed is the use of platelet derived growth factor for the enhancement of wound healing wherein the growth factor is either singularly or multiply dosed on a single day, rather than multiply dosed over a number of days. Also disclosed are pharmaceutical compositions comprising platelet derived growth factor.

15 Claims, 3 Drawing Sheets

USE OF PLATELET DERIVED GROWTH FACTOR TO ENHANCE WOUND HEALING

CROSS-REFERENCE TO RELATED APPLICATIONS

This application is a continuation of U.S. patent application Ser. No. 08/220,947, filed Mar. 31, 1994, now abandoned which is a continuation of U.S. patent application Ser. No. 07/738,760, filed Aug. 1, 1991, now abandoned which is a continuation-inpart of U.S. patent application Ser. No. 07/616,281, filed Nov. 20, 1990, now abandoned.

BACKGROUND OF THE INVENTION

1. Field of Invention

This invention relates to the treatment of ocular wounds. Ocular wounds which may be treated according to the present invention include, but are not limited to: persistent corneal defects; incisions for cataract extractions; corneal transplants; laser sculpturing of the cornea (including excimer lasers); incisions for vitreal or retinal surgery; incisions for implanting intraocular or intrastromal lenses; and scratches, burns or abrasions. For purposes of the present specification, ocular wounds such as those enumerated above which may be treated according to the present invention shall hereinafter collectively be referred to as "ocular wounds."

2. Description of Related Art

Growth factors are a family of low molecular weight proteins which have recently been shown to possess the ability to stimulate both the repair and maturation of tissues. Different growth factors act upon different types of tissue and in differing degrees. Examples of growth factors include epidermal growth factor (EGF), fibroblast growth factor (FGF), insulin-like growth factor (IGF), and platelet derived growth factor (PDGF).

A number of growth factors have had application in wound healing. A general discussion of growth factors useful in dermal wound healing may be found in an article by George A. Ksander in *Annual Reports in Medicinal Chemistry*, 24:223–232 (1989) and a discussion on the effects of growth factors on corneal tissue may be found in an article by D. Gospodarowicz and L. Giguere in Chapter. 3 of "Cell Biology of the Eye" (ed. David S. McDevitt), New York: Academic Press, 1982.

EGF has been the growth factor most predominantly used in healing abraided eyes. In general, EGF given four times a day (QID) over a period of days increases the rate of healing. To be most effective, EGF is dosed QID until the wound is completely healed, usually 3–4 days. Other types of growth factors, such as FGF and IGF, but not PDGF, have also been utilized in the same or similar dosing regime.

PDGF has primarily been studied in the context of dermal wound healing and has demonstrated an enhancement in collagen synthesis, as well as an increase of leukocytes in the wound area; however, an even greater activity in the area of a wound site has been demonstrated using combinations of PDGF+IGF and PDGF+EGF (Lynch, S. E. et al., *Proc. Nat'l Acad. Sci.*, 84:7696–7700 (1987)). These types of experiments have utilized dosing regimes which emphasize 'multiple applications over a period of weeks and/or the extended presence of a factor at the wound site. PDGF has not been used in connection with ocular wounds, except by Nakada, et al., *Invest. Ophthal. Vis. Sci.*, 31(4):54 (1990), in a multiple dosing format.

SUMMARY OF THE INVENTION

The present invention is based on the unexpected finding that PDGF may be used to enhance ocular wound healing by dosing on a single day rather than by multiple dosing over a period of days as is currently the case with EGF. PDGF dosed QID over a period of days generates a healing response which is indistinguishable from that seen with EGF (see FIG. 1); however, it has now been found that PDGF need only be given once to enhance ocular wound healing.

The present invention is directed to methods and compositions for the enhancement of ocular wound healing, particularly as applied to corneal wound healing. In the present invention, PDGF will preferably be topically applied using a suitable vehicle and may be formulated as solutions, suspensions, emulsions (dispersions), or in other suitable dosage forms.

DETAILED DESCRIPTION OF THE INVENTION

PDGF is known and commercially available, for example, from Creative Biomolecules (Hopkinton, Mass.). The biology of PDGF is generally discussed in an article by Ross, et al. in *Cell*, 46:155–169 (1986), which is hereby incorporated by reference herein.

As indicated in the Ross, et al. article, PDGF from human platelets is found as a heterodimer of two similar protein chains which have been termed A and B. Using recombinant DNA techniques known to those skilled in the art, PDGF may be produced as the naturally-occurring heterodimer (A-B) or as either the B-B or A-A homodimers (hereinafter respectively referred to as PDGF-AB, PDGF-BB, and PDGF-AA). Hereinafter in the present specification, the term "PDGF" shall refer to PDGF-AB, PDGF-BB, or PDGF which comprises various combinations of PDGF-AB, PDGF-BB, or PDGF-AA unless otherwise specified. It has been found that PDGF-AA cannot be utilized according to the method of the present invention, but both PDGF-AB and PDGF-BB may be utilized.

Without intending to be bound by any theory, it appears that PDGF is useful in the treatment of ocular wounds by acting on corneal stromal fibroblasts, causing them to secrete an additional factor which subsequently stimulates the corneal epithelial cells. Other possibilities include, but are not limited to, direct stimulation of epithelial cells or epithelial cell stimulation through neural pathways.

For use in treating ocular wounds, the therapeutically effective concentration of PDGF is in the range of about 0.001 to about 100 ug/ml and a typical dose for topical application is in the range of about 0.010 to about 0.060 ml. The preferred concentration of PDGF is about 25.0 ug/ml, with a preferred topical dose of 0.05 ml.

Figure 3:
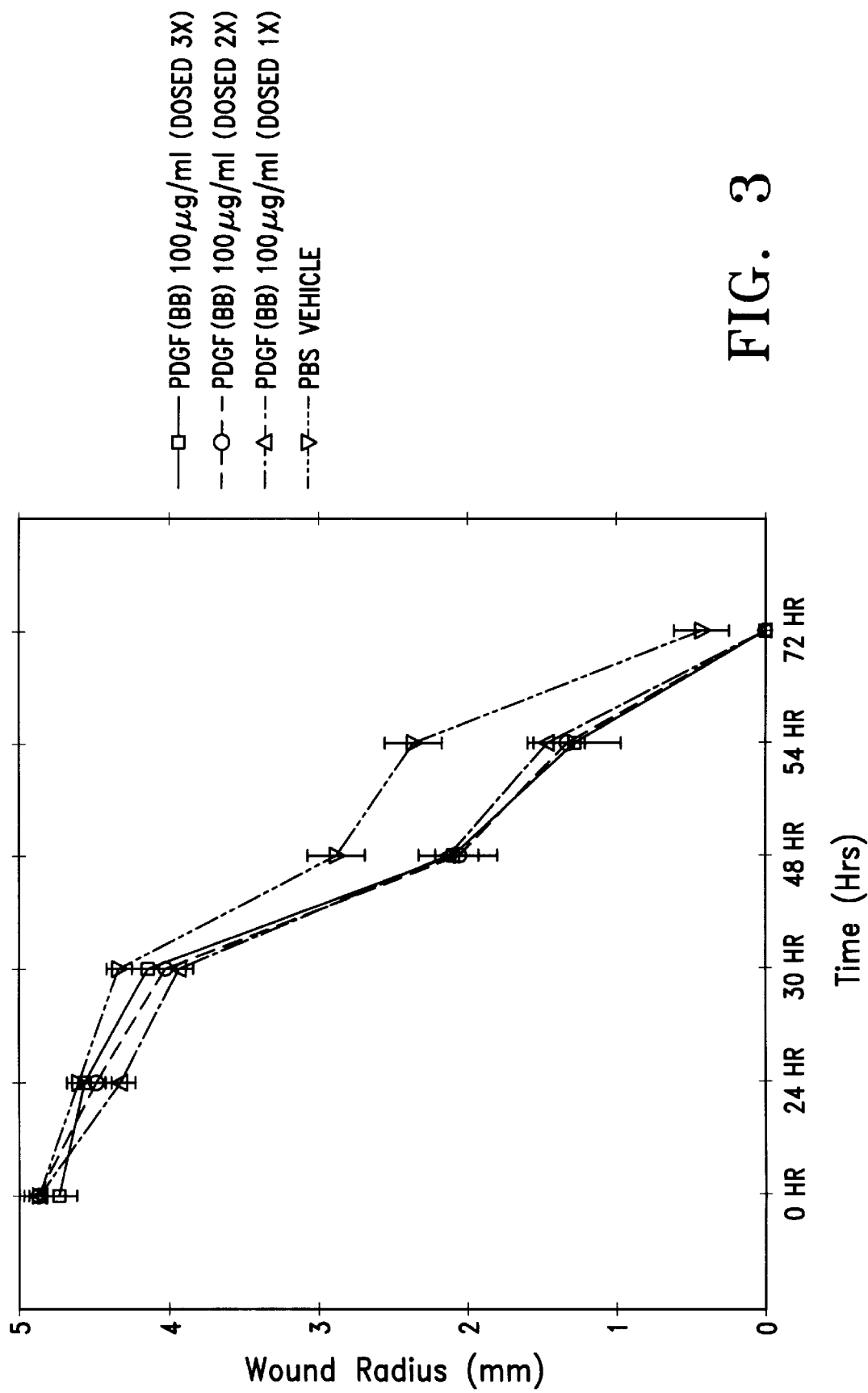
FIG. 3 is a graph comparing the effect of one, two, and three doses (Day 0 only) of PDGF (100 ug/ml) on the reduction of wound radius over time.

The pharmaceutical compositions of the present invention may be applied to wounds on a single day to enhance the healing rate. Although one application is generally sufficient, two or three applications are preferred to insure that an adequate amount of POGF remains in the eye and is not washed away in tears. As shown in FIG. 3, there is no discernible change in wound closure rate whether PDGF is dosed once, twice or three times on a single day.

The following examples are presented to illustrate further various aspects of the present invention, but are not intended to limit the scope of the invention in any respect.

EXAMPLE 1

The following are representative examples of useful compositions of the present invention.

| Liquid Medium | PDGF Concentration (ug/ml) |
|---|---|
| A. PBS | 0.001–100 |
| B. *VISCOAT ® | 0.001–100 |
| C. **BSS ® | 0.001–100 |

*VISCOAT ® is a visco-elastic composition and is available from Alcon Surgical, Inc. (Ft. Worth, Texas).
**BSS ® is a sterile physiological balanced salt solution and is available from Alcon Surgical, Inc..

The PDGF is solubilized in the liquid medium and, for composition A, the osmolality of the resultant solution is adjusted to approximately 300 milliOsmolal per kilogram (mOsm/kg). The compositions are either prepared under sterile conditions or sterilized by standard procedures such as sterile filtration after their preparation and prior to their use.

EXAMPLE 2

The following composition represents a preferred composition for treating ocular wounds.

| Ingredient | g/l |
|---|---|
| NaCl | 6.51957 |
| KCl | 0.359338 |
| CaCl$_2$*2H$_2$O | 0.15290 |
| MgCl$_2$*6H$_2$O | 0.15851 |
| NaH$_2$PO$_4$*2H$_2$O | 0.10320 |
| NaHCO$_3$ | 2.45309 |
| Glucose | 0.90260 |
| HCl or NaOH | to adjust pH to approx. 7.4 |
| Water | Q.S |

To this composition is added 0.010 mg/l of PDGF. The composition is either prepared under sterile conditions or sterilized after its preparation and prior to its use.

EXAMPLE 3

The comparative effectiveness of EGF, PDGF, and IGF on the rate of ocular wound healing was evaluated by determining the rate of resurfacing of the cornea with epithelial cells after a portion of the corneal epithelium was removed. A total of 16 New Zealand white rabbits were used in the study (4 rabbits per group) and the procedure for each rabbit was identical, except for the treatment.
Procedure After each rabbit was anesthetized and its upper and lower eyelashes trimmed, the epithelial cells were removed by scraping with a corneal gill knife. The scraping extended to within 1.0 to 1.5 mm of the limbus. This procedure produced a circular denuded area of approximately 10 mm in diameter. The procedure was repeated for the left eye. The corneas were then stained with fluorescein and photographed. Subsequent to the photograph, the corneas were topically dosed with 0.05 ml of the appropriate growth factor or PBS control. The growth factors were solubilized in PBS in the following concentrations: EGF=100 ug/ml; PDGF×100 ug/ml; IGF=10 ug/ml. Each rabbit was then returned to its cage and allowed to recover. During its recovery from anesthesia, each rabbit was observed every 15–20 minutes.

Figure 1:
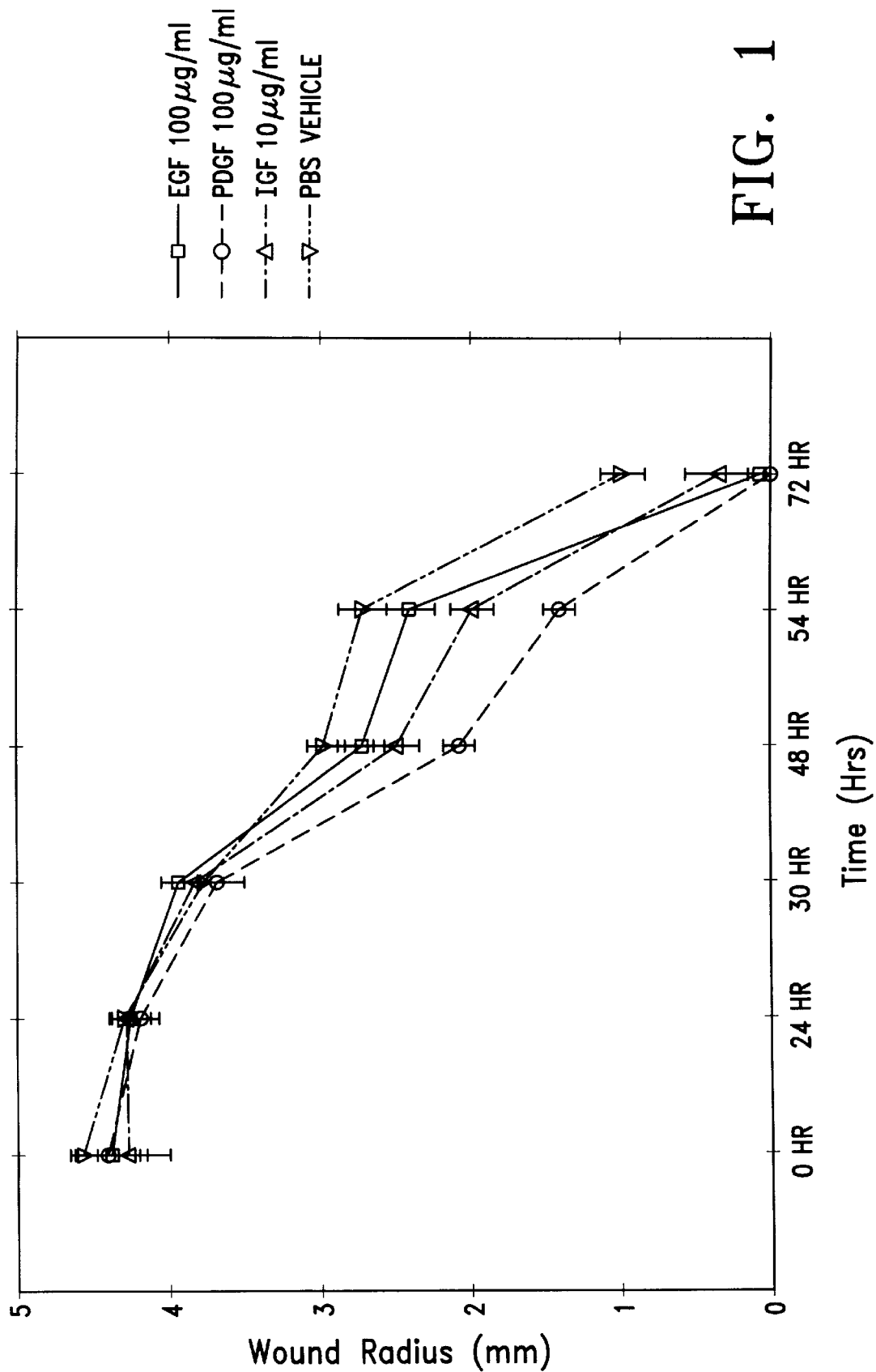
FIG. 1 is a graph comparing the effect of EGF (100 micrograms per milliliter (ug/ml)), PDGF (100 ug/ml), IGF (10 ug/ml), and phosphate buffered saline (PBS), as control, on the reduction of wound radius over time. EGF, PDGF, IGF, and PBS were all administered QID for three days.

Dosing was continued QID for three days and staining and photography of the corneas were repeated at 24, 30, 48, 54 and 72 hours after surgery. The results of the study are graphically illustrated in FIG. 1. The results show that rabbit corneas will heal without the use of growth factors but that addition of PDGF(-0-), IGF (-Δ-), or EGF (-∇-) results in an enhanced healing rate, as compared to the control (-∇-). Moreover, the PDGF treated wound shows a faster rate of wound radius reduction than either the IGF or EGF treated wounds.

EXAMPLE 4

In a study similar to that of Example 3, EGF (100 ug/ml) and PDGF (100 ug/ml) were each dosed three times on the day of surgery (Day 0) only, to determine whether there was a sustained effect. Periodic observation of the rabbits was maintained for 72 hours after surgery. A total of 15 New Zealand white rabbits were used in this study (5 rabbits per group) and the procedure of Example 3 was used, except that the rabbits were treated only on the day of surgery.

Figure 2:
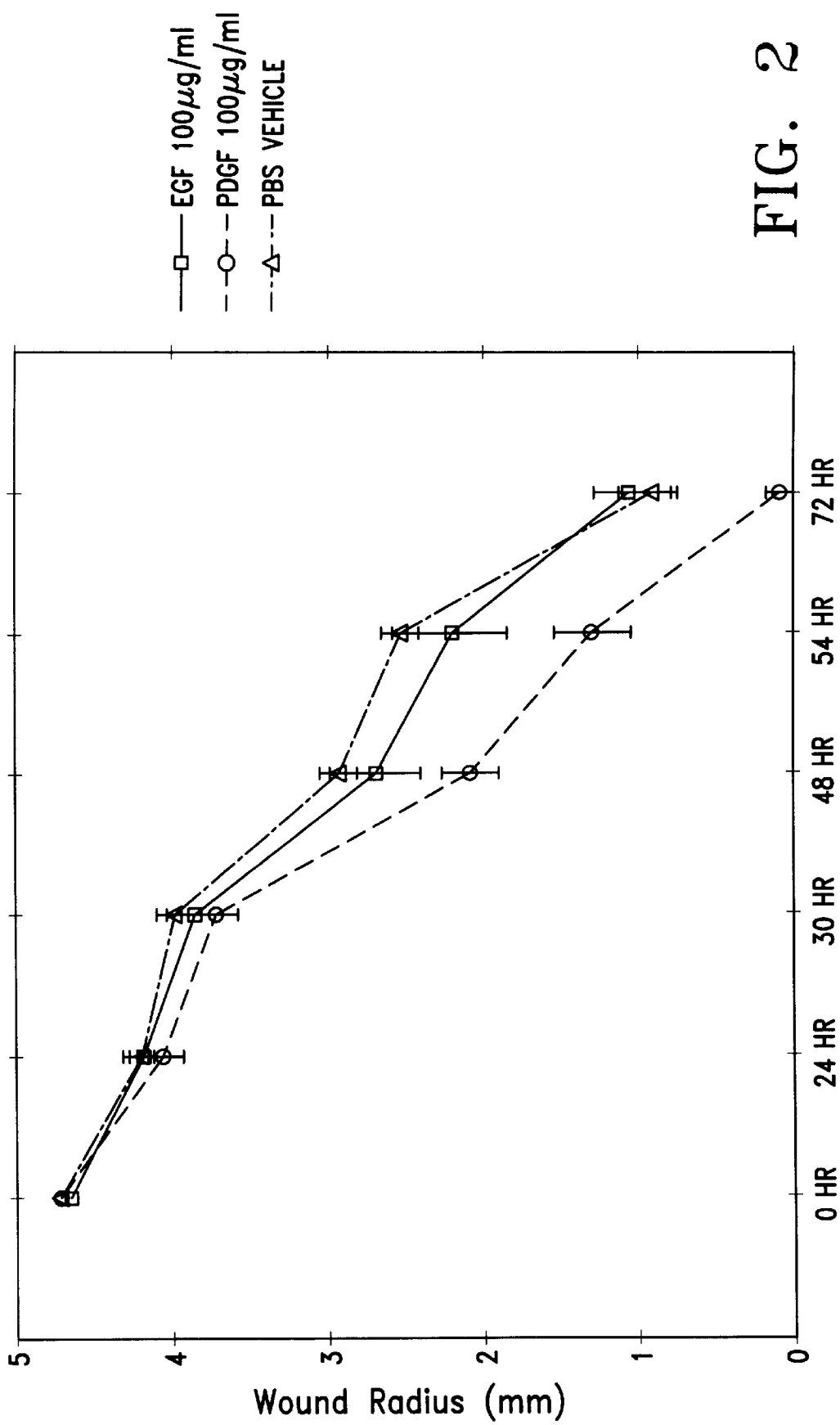
FIG. 2 is a graph comparing the effect of EGF (100 ug/ml), PDGF (100 ug/ml), and PBS on the reduction of wound radius over time. EGF, PDGF, and PBS were administered three times on Day 0 only.

The results, graphically illustrated in FIG. 2, show that PDGF has a sustained effect on wound healing while EGF does not. At 72 hours after surgery, the wounds treated with PDGF on the day of surgery had completely healed, whereas the wounds treated with EGF had an average radius of 1 mm.

EXAMPLE 5

A study comparing the effectiveness of one, two and three doses of PDGF (100 ug/ml) was also conducted using the procedure of Example 3. A total of 16 New Zealand white rabbits were used (4 rabbits per group). The results, graphically illustrated in FIG. 3, show that there is no change in the rate of wound closure regardless of how many times the rabbits were dosed with PDGF on the day of surgery.

What is claimed is:

1. A method for enhancing the rate of corneal wound healing comprising topically administering to a corneal wound an amount of substantially pure PDGF effective to enhance corneal wound healing.

2. The method of claim 1 wherein the PDGF is PDGF-AB.

3. The method of claim 1 wherein the PDGF is PDGF-BB.

4. The method of claim 1, wherein about 0.5 ml of a composition comprising between about 0.001 and about 100 μg/ml of PDGF is administered to the corneal wound.

5. The method of claim 4, wherein about 0.5 ml of a composition comprising about 25 μg/ml of PDGF is administered to the corneal wound.

6. The method of claim 1, wherein the PDGF is administered 1–3 times in a single day.

7. The method of claim 1, wherein the PDGF is administered in a composition which additionally comprises:

a solution containing between about 130 and about 180 mM sodium ions, between about 3 and about 10 mM potassium ions, between about 1 and about 5 mM calcium ions, between about 0.5 and about 4 mM magnesium ions, between about 10 and about 50 mM bicarbonate ions, and between about 2 and about 10 mM dextrose; and wherein said solution has a pH in the range of about 6.8 to about 8.0 and an osmolality in the range of about 250 to about 350 mOsm/kg.

8. The method of claim 7 wherein the PDGF is present at a concentration in the range of about 0.001 to about 100 ug/ml.

9. The method of claim 8 wherein the PDGF is present at a concentration of 25 ug/ml.

10. The method of claim 7 wherein the PDGF is PDGF-AB.

11. The method of claim 7 wherein the PDGF is PDGF-BB.

12. The method of claim 6 wherein the PDGF is administered once.

13. The method of claim 6 wherein the PDGF is administered twice.

14. The method of claim 6 wherein the PDGF is administered three times.

15. A method of enhancing the rate of corneal wound healing, comprising topically administering to a corneal wound in a single application an amount of substantially pure PDGF effective to enhance the corneal wound healing.

* * * * *